(12) United States Patent
O'Donnell et al.

(10) Patent No.: US 10,888,304 B2
(45) Date of Patent: Jan. 12, 2021

(54) REAL-TIME PHOTOACOUSTIC AND ULTRASOUND IMAGING SYSTEM AND METHOD

(71) Applicant: University of Washington, Seattle, WA (US)

(72) Inventors: Matthew O'Donnell, Seattle, WA (US); Thu-Mai Nguyen, Seattle, WA (US); Chen-Wei Wei, Seattle, WA (US); Jinjun Xia, Seattle, WA (US); Ivan Pelivanov, Seattle, WA (US); Soon Joon Yoon, Seattle, WA (US)

(73) Assignee: University of Washington, Seattle, WA (US)

( * ) Notice: Subject to any disclaimer, the term of this patent is extended or adjusted under 35 U.S.C. 154(b) by 465 days.

(21) Appl. No.: 15/308,828

(22) PCT Filed: May 11, 2015

(86) PCT No.: PCT/US2015/030207
§ 371 (c)(1),
(2) Date: Nov. 3, 2016

(87) PCT Pub. No.: WO2015/175431
PCT Pub. Date: Nov. 19, 2015

(65) Prior Publication Data
US 2017/0079622 A1    Mar. 23, 2017

Related U.S. Application Data

(60) Provisional application No. 61/991,731, filed on May 12, 2014.

(51) Int. Cl.
*A61B 8/08*         (2006.01)
*A61B 5/00*         (2006.01)
(Continued)

(52) U.S. Cl.
CPC .......... *A61B 8/5261* (2013.01); *A61B 5/0035* (2013.01); *A61B 5/0095* (2013.01);
(Continued)

(58) Field of Classification Search
None
See application file for complete search history.

(56) References Cited

U.S. PATENT DOCUMENTS 7,068,867 B2    6/2006    Adoram et al.
8,298,144 B2 *  10/2012   Burcher ............... A61B 5/0059
                                                         600/407
(Continued)

OTHER PUBLICATIONS

Ermilov, S.A., et al., "Development of Laser Optoacoustic and Ultrasonic Imaging System for Breast Cancer Utilizing Handheld Array Probes," Proceedings of SPIE—The International Society for Optical Engineering, Jan. 2009, Photons Plus Ultrasound: Imaging and Sensing 2009, edited by A. Oraevsky et al. in Proc. of SPEI vol. 7177, 717703.
(Continued)

*Primary Examiner* — Oommen Jacob
*Assistant Examiner* — Shahdeep Mohammed
(74) *Attorney, Agent, or Firm* — Christensen O'Connor Johnson Kindness PLLC (57) ABSTRACT

Methods and system for producing combined photoacoustic/ultrasonic image frames use a low-power narrow beam laser to direct sequential pulses along a path overlying an internal region of interest. Photoacoustic responses are received and used to generate sub-frames. Between each of the laser pulses a plurality of ultrasound pulse-echo beams are sequentially emitted towards the region of interest, and the reflections are received and used to generate ultrasound sub-frames. The photoacoustic sub-frames are combined to produce a photoacoustic frame, and the ultrasound sub-frames are combined to produce an ultrasound frame. The
(Continued)

photoacoustic and ultrasound frames are combined to produce an image frame. The method and system are suitable for producing real-time, high-contrast video.

19 Claims, 5 Drawing Sheets

(51) Int. Cl.
  *A61B 8/00* (2006.01)
  *A61B 8/14* (2006.01)
(52) U.S. Cl.
  CPC .............. *A61B 8/0841* (2013.01); *A61B 8/14* (2013.01); *A61B 8/4416* (2013.01); *A61B 8/4483* (2013.01); *A61B 8/463* (2013.01)

(56) References Cited

U.S. PATENT DOCUMENTS

| | | | |
|---|---|---|---|
| 8,353,833 B2 | 1/2013 | Dogra et al. | |
| 2009/0156932 A1* | 6/2009 | Zharov | A61B 5/0059 600/437 |
| 2010/0094134 A1 | 4/2010 | Zhu et al. | |
| 2012/0253180 A1 | 10/2012 | Emelianov et al. | |
| 2013/0039147 A1 | 2/2013 | Witte et al. | |
| 2013/0109950 A1* | 5/2013 | Herzog | A61B 8/0825 600/407 |

OTHER PUBLICATIONS

International Search Report and Written Opinion dated Aug. 17, 2015, issued in corresponding Application No. PCT/US2015/030207, filed May 11, 2015, 8 pages.
Alqasemi, U., et al., "FPGA-Based Reconfigurable Processor for Ultrafast Interlaced Ultrasound and Photoacoustic Imaging," IEEE Transactions on Ultrasonics, Ferroelectrics, and Frequency Control 59(7):1344-1353, Jul. 2012. (Author Manuscript provided, PMCID:PMC5079523, available in PMC Oct. 25, 2016, 28 pages.).
Alqasemi, U., et al., "Real-Time Co-Registered Ultrasound and Photoacoustic Imaging System Based on FPGA and DSP Architecture," Proceedings of SPIE 7899, Photons Plus Ultrasound: Imaging and Sensing 2011, Mar. 2011, pp. 78993S-1-78993S12.
"American National Standard for Safe Use of Lasers," American National Standard, ANSI® Z136.1-2007, Revision of ANSI Z136.1-2000, 22 pages.
Bavu, E., et al., "Noninvasive In Vivo Liver Fibrosis Evaluation Using Supersonic Shear Imaging: A Clinical Study on 113 Hepatitis C Virus Patients," Ultrasound in Medicine and Biology 37(9):1361-1373, Sep. 2011.
Bowen, T., "Radiation-Induced Thermoacoustic Soft Tissue Imaging," Proceedings of the Ultrasonics Symposium, Oct. 14-16, 1981, Chicago, pp. 817-822.
Buehler, A., et al., "Real-Time Handheld Multispectral Optoacoustic Imaging," Optics Letters 38(9):1404-1406, May 2013.
Caturelli, E., et al., "Ultrasound Guided Fine Needle Biopsy of Early Hepatocellular Carcinoma Complicating Liver Cirrhosis: A Multicentre Study," Gut 53(9):1356-1362, Sep. 2004.
Dean, J., et al., "Real-Time Photoacoustic Data Acquisition With Philips iU22 Ultrasound Scanner," Proceedings of SPIE 6856, Photons Plus Ultrasound: Imaging and Sensing 2008: The Ninth Conference on Biomedical Thermoacoustics, Optoacoustics, and Acousto-Optics, Jan. 20-23, 2008, San Jose, Calif., pp. 685622-1-685622-11.
Emelianov, S.Y., et al., "Photoacoustics for Molecular Imaging and Therapy," Physics Today 62(8):34-39, May 2009. (Author Manuscript provided, PMCID:PMC2879661, available in PMC Jun. 2, 2010, 13 pages.).
Ermilov, S.A., et al., "Development of Laser Optoacoustic and Ultrasonic Imaging System for Breast Cancer Utilizing Handheld Array Probes," Proceedings of SPIE 7177, Photons Plus Ultrasound: Imaging and Sensing 2009, Feb. 2009, pp. 717703-1-717703-10.
Guo, Z., et al., "On the Speckle-Free Nature of Photoacoustic Tomography," Medical Physics 36(9):4084-4088, Sep. 2009.
Homan, K., "Prospects of Molecular Photoacoustic Imaging at 1064 nm Wavelength," Optics Letters 35(15):2663-2665, Aug. 2010. (Author Manuscript provided, PMCID:PMC3059192, available in PMC Mar. 16, 2011, 8 pages.).
Homan, K.A., "Silver Nanoplate Contrast Agents for In Vivo Molecular Photoacoustic Imaging," ACS Nano 6(1):641-650, Jan. 2012.
Huang, S.-W., et al., "Differential-Absorption Photoacoustic Imaging," Optics Letters 34(16):2393-2395, Aug. 2009.
Ke, H., et al., "Performance Characterization of an Integrated Ultrasound, Photoacoustic, and Thermoacoustic Imaging System," Journal of Biomedical Optics 17(5):056010, May 2012, 7 pages.
Kim, C., et al., "Handheld Array-Based Photoacoustic Probe for Guiding Needle Biopsy of Sentinel Lymph Nodes," Journal of Biomedical Optics 15(4):046010, Jul.-Aug. 2010, 4 pages.
Kolkman, R.G.M., et al., "Real-Time In Vivo Photoacoustic and Ultrasound Imaging," Journal of Biomedical Optics 13(5):050510-1-050510-3, Sep.-Oct. 2008.
Kruger, R.A., et al., "Thermoacoustic Molecular Imaging of Small Animals," Molecular Imaging 2(2):113-123, Apr. 2003.
Ku, G., and L.V. Wang, "Scanning Microwave-Induced Thermoacoustic Tomography: Signal, Resolution, and Contrast," Medical Physics 28(1):4-10, Jan. 2001.
Larson-Smith, K., and D.C. Pozzo, "Pickering Emulsions Stabilized by Nanoparticle Surfactants," Longmuir 28(32):11725-11732, Aug. 2012.
Li, C., and L.V. Wang, "Photoacoustic Tomography and Sensing in Biomedicine," Physical Medical Biology 54(19):R59-R97, Oct. 2009. (Author Manuscript provided, PMCID:PMC2872141, available in PMC May 18, 2010, 52 pages.).
McMillan, A.M., et al., "Ultrasound Guided Corticosteroid Injection for Plantar Fasciitis: Randomised Controlled Trial," BMJ 344:e3260, May 2012, 12 pages.
Montilla, L.G., et al., "Real-Time Photoacoustic and Ultrasound Imaging: A Simple Solution for Clinical Ultrasound Systems With Linear Arrays," Physics in Medicine and Biology 58(1):N1-N12, Jan. 2013.
Natarajan, S., et al., "Clinical Application of a 3D Ultrasound-guided Prostate Biopsy System: Biopsy Tracking and Lesion Targeting via Real-time MRI/Ultrasound Fusion," Urology Oncology 29(3):334-342, May-Jun. 2011. (Author Manuscript provided, PMCID:PMC3432280, available in PMC Sep. 1, 2012, 19 pages.).
Niederhauser, J.J., et al., "Combined Ultrasound and Optoacoustic System for Real-Time High-Contrast Vascular Imaging In Vivo," IEEE Transactions on Medical Imaging 24(4):436-440, Apr. 2005.
O'Donnell, M., et al., "Can Molecular Imaging Enable Personalized Diagnostics? An Example Using Magnetomotive Photoacoustic Imaging," Annual Biomedical Engineering 41(11):2237-2247, Nov. 2013. (Author Manuscript provided, PMCID:PMC3855400, available in PMC Nov. 1, 2014, 20 pages.).
Palmeri, M.L., et al., "Quantifying Hepatic Shear Modulus In Vivo Using Acoustic Radiation Force," Ultrasound in Medicine and Biology 34(4):546-558, Apr. 2008.
Razansky, D., et al., "Volumetric Ral-Time Multispectral Optoacoustic Tomography of Biomarkers," Nature Protocols 6(8):1121-1129, Jul. 2011.
Sauer, G., et al., "Ultrasound-Guided Large-Core Needle Biopsies of Breast Lesions: Analysis of 962 Cases to Determine the Number of Samples for Reliable Tumour Classification," British Journal of Cancer 92(2):231-235, Jan. 2005.
Su, J., et al., "Photoacoustic Imaging of Clinical Metal Needles in Tissue," Journal of Biomedical Optics 15(2):021309, Mar.-Apr. 2010, 6 pages.
Tanter, M., et al., "Quantitative Assessment of Breast Lesion Viscoelasticity: Initial Clinical Results Using Supersonic Shear Imaging," Ultrasound in Medicine and Biology 34(9):1373-1386, Sep. 2008.

(56) References Cited

OTHER PUBLICATIONS

Taruttis, A., et al., "Fast Multispectral Optoacoustic Tomography (MSOT) for Dynamic Imaging of Pharmacokinetics and Biodistribution in Multiple Organs," PLoS One 7(1):e30491, Jan. 2012, 6 pages.

Wang, L., et al., "Video-Rate Functional Photoacoustic Microscopy at Depths," Journal of Biomedical Optics 17(10):106007, Oct. 2012, 6 pages.

Wei, C.-W., et al., "Real-Time Integrated Photoacoustic and Ultrasound (PAUS) Imaging System to Guide Interventional Procedures: Ex Vivo Study," IEEE Trans Ultrason Ferroectr Freq Control 62(2):319-328, Feb. 2015. (Author Manuscript provided, PMCID:PMC4610852, available in PMC Oct. 19, 2015, 21 pages.).

Wei, C.-W., et al., "Magnetomotive Photoacoustic Imaging: In Vitro Studies of Magnetic Trapping With Simultaneous Photoacoustic Detection of Rare Circulating Tumor Cells," Journal of Biophotonics 6(6-7):513-522, Jun. 2013. (Author Manuscript provided, PMCID:PMC3705769, available in PMC Jun. 1, 2014, 27 pages.).

Wei, C.-W., et al., "Trapping and Dynamic Manipulation of Polystyrene Beads Mimicking Circulating Tumor Cells Using Targeted Magnetic/Photoacoustic Contrast Agents," Journal of Biomedical Optics 17(10):101517, Oct. 2012, 7 pages.

Wilson, K.E., et al., "Acoustic and Photoacoustic Molecular Imaging of Cancer," Journal of Nuclear Medicine 54(11):1851-1854, Nov. 2013. (Author Manuscript provided, PMCID:PMC4084699, available in PMC Jul. 7, 2014, 12 pages.).

Xi, L., et al., "Photoacoustic Imaging Based on MEMS Mirror Scanning," Optics Express 18(23):1278-1283, Nov. 2010.

Xia, J., et al., "Comparison of PA Imaging by Narrow Beam Scanning and One-Shot Broad Beam Excitation," Proceedings of SPIE 7899, Photons Plus Ultrasound: Imaging and Sensing 2011, Mar. 2011, 78991L-1-78991L-7.

Xia, J., et al., "Photoacoustic Imaging Using Narrow Beam Scanning," Proceedings of the IEEE International Ultrasonics Symposium, Oct. 18-21, 2011, Orlando, Fla., pp. 2380-2383.

Yang, J.-M., et al., "Simultaneous Functional Photoacoustic and Ultrasonic Endoscopy of Internal Organs In Vivo," Nature Medicine 18(8):1297-1302, Aug. 2012. (Author Manuscript provided, PMCID:PMC3885361, available in PMC Jan. 8, 2014, 15 pages.).

Yuan, J., et al., "Real-Time Photoacoustic and Ultrasound Dual-Modality Imaging System Facilitated With Graphics Processing Unit and Code Parallel Optimization," Journal of Biomedical Optics 18(8):086001, Aug. 2013, 6 pages.

Zheng, F., et al., "Laser-Scanning Photoacoustic Microscopy With Ultrasonic Phased Array Transducer," Biomedical Optics Express 3(11):2694-2699, Nov. 2012.

\* cited by examiner

REAL-TIME PHOTOACOUSTIC AND ULTRASOUND IMAGING SYSTEM AND METHOD

STATEMENT OF GOVERNMENT LICENSE RIGHTS

This invention was made with the support of the United States government under Grant number R01 EB016034 by the National Institutes of Health. The government has certain rights in the invention.

BACKGROUND

Photoacoustic imaging complements clinical ultrasound by adding optical absorption as a contrast mechanism at spatial resolutions comparable to ultrasound for penetration depths up to a few centimeters. Using the same transducers and imaging electronics, it can provide molecular information absent from ultrasound images. Ultrasound-guided photoacoustic imaging can have several clinical applications related to imaging the vasculature (exploiting hemoglobin contrast); detecting molecularly targeted, nanoscale contrast agents; and guiding interventional procedures. An integrated scan format in which photoacoustic/ultrasound image frames are interleaved at real-time rates is needed for optimal translation of this technology to the clinic.

Integrated photoacoustic/ultrasound systems have been developed as a research tool. Typically, high-pulse-energy (tens to hundreds of millijoules per pulse) Q-switched lasers are required to produce high signal-to-noise ratio (SNR) photoacoustic signals induced by nanosecond pulses. However, these laser sources are generally not cost effective, massive (usually >1 m long with a bulky power unit), and difficult to maintain. In addition, their low pulse repetition frequency (PRF) can severely limit image frame rates for real-time operation, hindering integration of photoacoustics with a real-time commercial ultrasound scanner for clinical applications. To facilitate clinical translation of interleaved photoacoustic/ultrasound imaging, a low-cost and portable laser is integrated with a commercial ultrasound scanner.

For example, portable fiber-amplified semiconductor-based lasers and laser diode-pumped Q-switched lasers are relatively inexpensive and output nanosecond pulses with repetition rates up to several hundreds of kilohertz. However, these lasers are not suitable for conventional photoacoustic imaging because the single pulse energies produced are quite low, in most cases from hundreds of microjoules up to a few millijoules. Such low energies distributed over an entire image volume of interest cannot generate photoacoustic signals with acceptable SNR characteristics for single-pulse operation. To produce acceptable optical fluence (energy per unit area) for high-SNR measurements, the beam must be focused to a small spot. This means the lateral extent of the image is quite limited. In addition, optical scattering is very strong for most biological tissues in the visible and near-infrared optical wavelength range, limiting light penetration, especially for a small diameter beam spot.

The SNR can be improved by averaging. However, the SNR improvement from averaging only increases as the square root of the number of pulses, and the PRF is limited by the acoustic time-of-flight to avoid range ambiguities (i.e., sources from multiple ranges delivering photoacoustic signals to the ultrasound array at the same time). For example, to image a 1-cm region, the laser pulse repetition interval (PRI) should be larger than the acoustic propagation time, $$PRI = \frac{1}{PRF} \geq \frac{\text{imaging range}}{\text{sound velocity}} = \frac{1 \text{ cm}}{1540 \text{ m/s}}$$

The maximum PRF is therefore approximately 154 kHz. Furthermore, laser safety regulations (maximum average power of 1 W/m$^2$) also limit the repetition rate for a given laser fluence. For example, the maximum fluence allowed for a 1-kHz laser is 1 mJ/cm$^2$, a value producing low optical intensities deep inside the body. Therefore, there is a tradeoff between SNR (related to laser fluence) and image frame rate (related to PRF).

As disclosed herein, these limitations may be overcome in part by combining the photoacoustic response of multiple laser pulses that are scanned over a region of interest. A high-repetition-rate (e.g., ~1 kHz), low-energy (e.g., a few millijoules) laser enables rapid scanning Photoacoustic signals induced by each laser shot are recorded to form a sub-frame of radio frequency (RF) data. Photoacoustic sub-frames corresponding to the narrow beam sub-frame can be reconstructed to show regional information near the laser scanning spot. The final photoacoustic image covering the complete scan area is synthetically reconstructed by combining all RF sub-frames. A real-time interleaved photoacoustic/ultrasound system with a frame rate of 30 Hz or greater is disclosed.

One or more of the present inventors have demonstrated photoacoustic imaging using beam scanning, as described in more detail in J. Xia, C.-W. Wei, I. M. Pelivanov, and M. O'Donnell, "Photoacoustic imaging using narrow beam scanning," in IEEE Int. Ultrasonics Symp., 2011, pp. 2380-2383, and in J. Xia, C.-W. Wei, L. Huang, I. M. Pelivanov, and M. O'Donnell, "Comparison of PA imaging by narrow beam scanning and one-shot broad beam excitation," Proc. SPIE, vol. 7899, Art. No. 78991L, 2011, each of which is hereby incorporated by reference in its entirety.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

A method for generating a combined photoacoustic and ultrasound image frame of an internal region of a body includes (i) irradiating a first location on the surface of the body with a laser pulse to illuminate the internal region, and using the corresponding photoacoustic response to generate a first photoacoustic sub-frame; (ii) sequentially transmitting ultrasound pulse-echo beams towards a first section of the internal region, and using the ultrasound reflections to generate a first set of ultrasound sub-frames of the internal region; (iii) irradiating a second location on the surface of the body with a laser pulse to illuminate the internal region, and using the corresponding photoacoustic response to generate a second photoacoustic sub-frame; (iv) sequentially transmitting ultrasound pulse-echo beams towards a second section of the internal region, and using the ultrasound reflections to generate a second set of ultrasound sub-frames of the internal region; combining the first and second photoacoustic sub-frames to generate a photoacoustic frame of the internal region, and combining the first and second sets of ultrasound sub-frames to generate an ultrasound frame of the internal region; and (v) combining the photoacoustic frame and the ultrasound frame to generate an image frame of the internal region of the body.

In an embodiment the laser pulses have energies of less than 10 mJ, and in embodiment the laser pulses have energies of less than 2 mJ. In an embodiment the laser pulses have a diameter of less than 3 mm.

In an embodiment the laser pulses have a wavelength between 400 and 1500 nm, and a fluence less than a wavelength-dependent fluence that would damage tissue. In an embodiment the fluence is less than 100 mJ/cm$^2$.

In an embodiment at least six ultrasound pulse-echo beams are directed towards the internal region after each laser pulse.

In an embodiment the laser pulses are produced by a laser diode-pumped Q-switched laser, and the ultrasound pulse-echo beams are generated with an ultrasound linear array that also receives the ultrasound reflections and the photoacoustic responses.

In an embodiment the ultrasound linear array is disposed in a probe, and the laser pulses are emitted from a distal face of the probe. The laser pulses may be transmitted to the probe by optical fibers extending along either side of the ultrasound linear array. In an embodiment the laser pulses are distributed from the laser to the optical fibers with a remote switching unit.

In an embodiment the methods described above are used to generate a real-time video of the internal region.

A method for generating a combined photoacoustic and ultrasound image of an internal region of a body includes irradiating the external surface of the body with sequential narrow-beam, lower power laser pulses that irradiate the internal region of the body, wherein the sequential laser pulses are directed to a plurality of different locations along a path on the external surface, and receiving photoacoustic signals from the body corresponding to the sequential laser pulses; between each of the sequential laser pulses, sequentially transmitting a plurality of ultrasound pulse-echo beams to the internal region of the body, and receiving ultrasound reflections of the plurality of ultrasound pulse-echo beams; generating a first set of sub-frames from the received photoacoustic signals; generating a second set of sub-frames from the received ultrasound reflections; and combining the first set of sub-frames with the second set of sub-frames to generate a combined photoacoustic and ultrasound image frame of the internal region of the body.

An imaging system for providing real-time images of an internal region of a body includes an ultrasound linear array configured to generate ultrasound pulses, to receive and process ultrasound reflection data, and to receive and process photoacoustic signals; a laser configured to generate narrow-beam laser pulses having a pulse energy of less than 5 mJ; a laser pulse distributor configured to receive laser pulses from the laser and to direct the pulses to a plurality of locations on a target; and a computer system configured to control the ultrasound linear array, the laser, and the laser pulse distributor, to receive processed ultrasound reflection data and photoacoustic signals from the ultrasound linear array, and to generate combined photoacoustic and ultrasound images from the received data and signals.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

A particular embodiment of an integrated scanning photoacoustic and ultrasound imaging system and method will now be described with reference to the drawings, wherein like numbers indicate like parts. In the embodiment shown in FIG. 1, a low-power, small-diameter beam, pulsed laser is scanned over a region of interest, and a photoacoustic sub-frame (or sub-image) response is recorded for each laser pulse, as discussed in more detail below. Between laser pulses several sequential ultrasound pulse-echo beams are formed close to the scanning laser beam location after each laser pulse, and pulse-echo sub-frame images are recorded.

There are two benefits of interleaving ultrasound beams between photoacoustic sub-frames: 1) the ultrasound information and the photoacoustic information are acquired at the same or nearly the same spatial location; this is especially important for imaging moving objects or monitoring fast changing dynamics; and 2) the dead-time between laser pulses (tens of microseconds photoacoustic recording for centimeters range versus the millisecond PRI for a kilohertz laser) is fully utilized, increasing the frame rate because ultrasound pulse-echo recordings do not have to wait until all photoacoustic recordings are finished. This novel method of interleaving ultrasound sub-frames between photoacoustic sub-frames enables the production of real-time interleaved photoacoustic/ultrasound images for deep imaging (up to several centimeters) with a frame rate greater than 30 Hz, thereby enabling the use of such combined images for clinical applications. Frame rates of 60 Hz or greater may be readily achieved in real-time to produce moving images of an internal region of interest.

For example, an integrated photoacoustic/ultrasound imaging system disclosed herein is suitable for clinical applications where co-registered photoacoustic/ultrasound is needed to provide real-time and precise monitoring with high-contrast images. As discussed below, the system disclosed herein has produced real-time video showing needle insertion into tissue and simulated therapeutic agent injection.

Ultrasound (only) image-guided needle monitoring has been used in clinical applications such as biopsy in prostate and breast, and therapeutic agent injection. Unfortunately, the quality of the ultrasound image is directly related to the orientation of the needle relative to the scan direction of the real-time image because the primary signal from a needle is the specular reflection from its surface. In many cases, proper orientation is problematic and tracking precision is lost because of the poor ultrasound contrast and additional artifacts associated with the needle. In addition, background scattering degrades image contrast, limiting the precision of the biopsy and injection.

However, photoacoustic signals from the needle are much less dependent on the orientation of the light source and less sensitive to needle-transducer orientation. In photoacoustic imaging the needle is a cylindrical acoustic source in the transducer imaging field. In ultrasound imaging, however, the needle is a reflector and usually scatters the probe ultrasound beam in a direction different from that of the incident ultrasound beam. As a result, photoacoustic imaging is less sensitive to transducer-target orientation compared with ultrasound imaging. Also, photoacoustic imaging exhibits higher contrast to monitor injected exogenous agents because of the speckle-free background, and the ability to easily label agents with molecular dyes of high optical absorption at the optical wavelength used for photoacoustic imaging.

Figure 1:
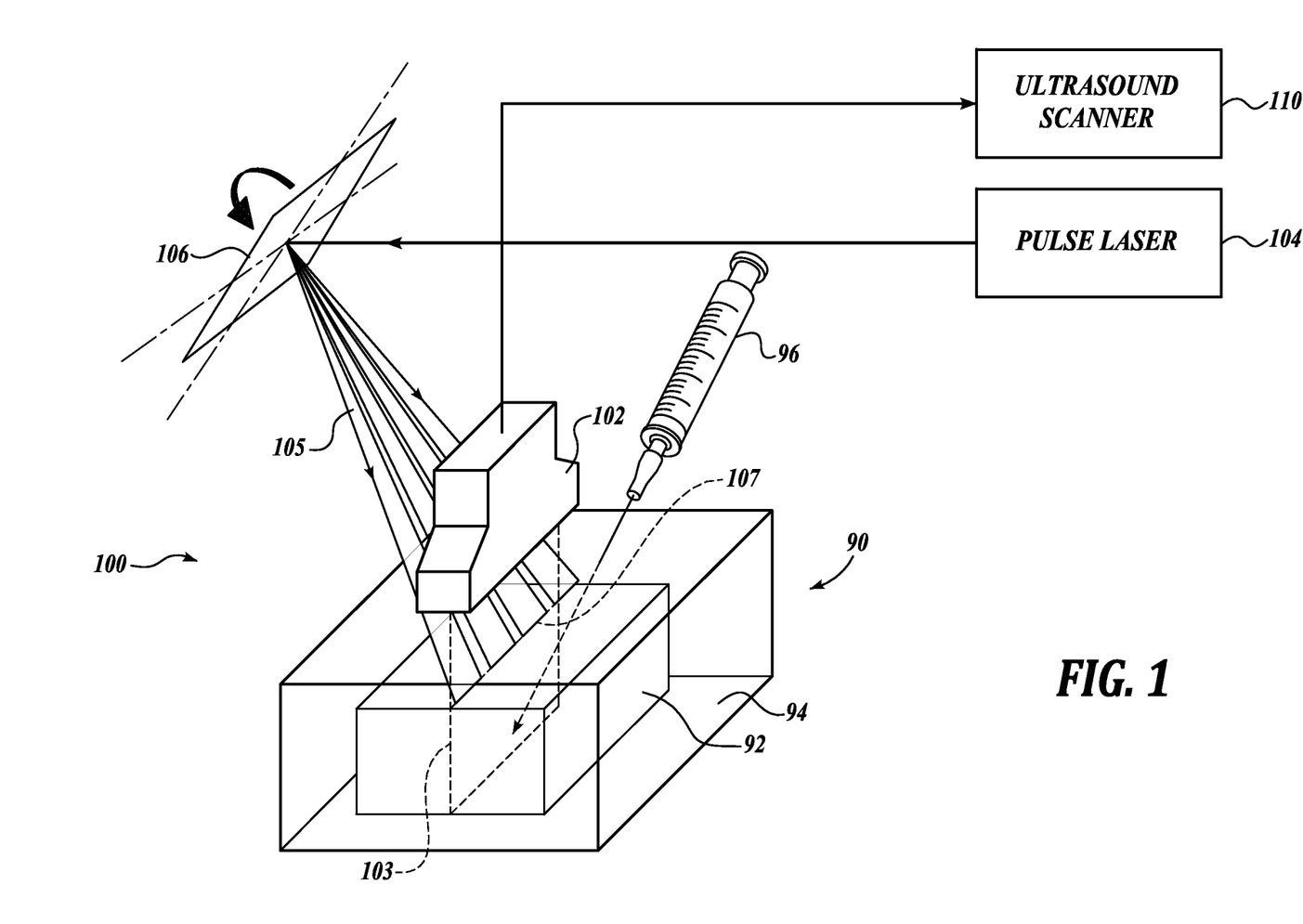
FIG. 1 is a schematic diagram of a testing arrangement with an integrated photoacoustic and ultrasound imaging system using a narrow beam pulsed laser scanning system in accordance with the present invention.
Figure 2:
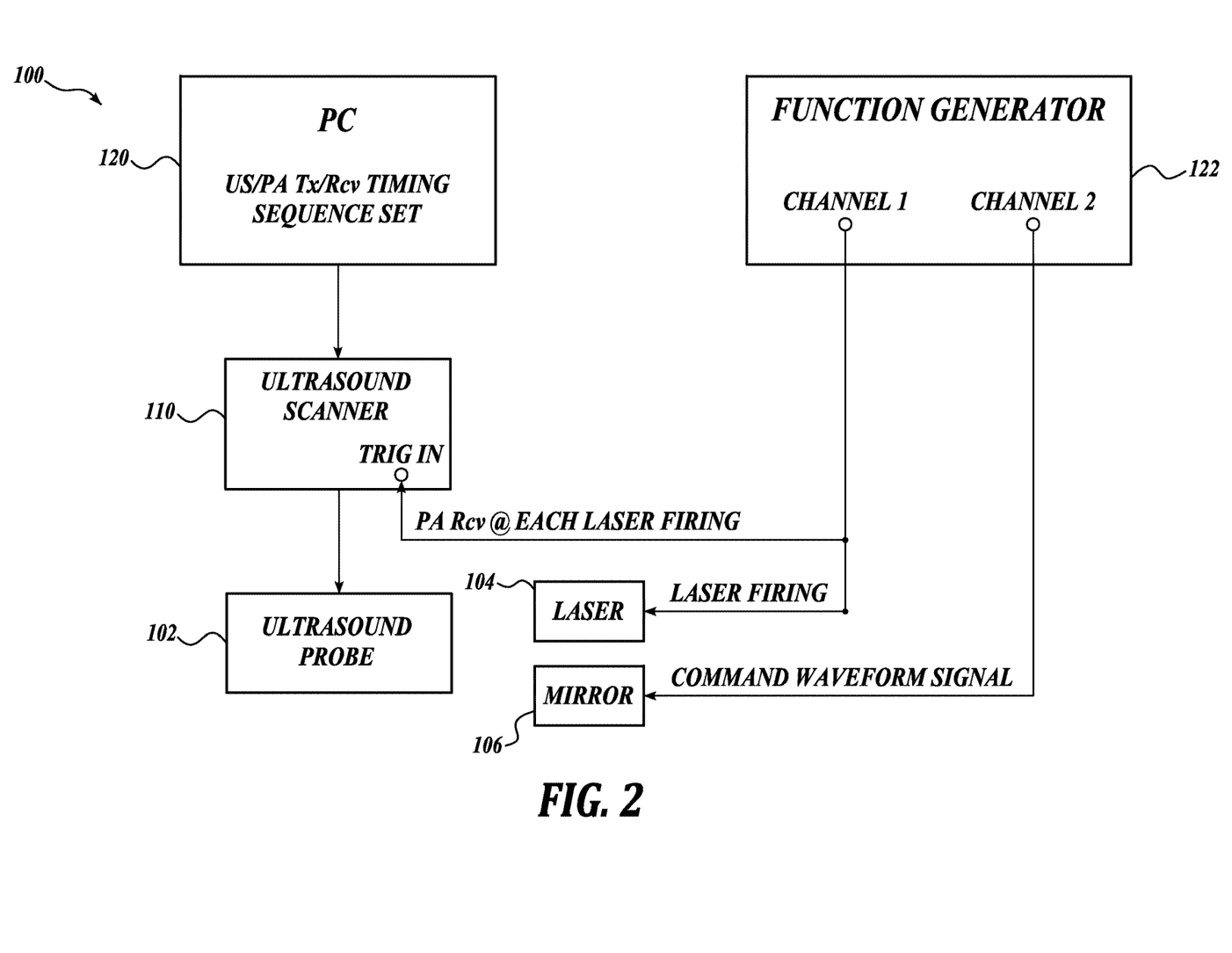
FIG. 2 is a block diagram for the imaging system shown in FIG. 1.

An experimental arrangement demonstrating image acquisition for an interleaved photoacoustic/ultrasound imaging system 100 in accordance with the present invention is shown schematically in FIG. 1. A block diagram of the system 100 is shown in FIG. 2.

The system 100 includes an ultrasound probe 102 having a linear array with 128 channels (e.g., AT8L12-5 50 mm, Broadsound Corp.; central frequency 9 MHz, bandwidth 5 to 12 MHz, 256 elements, 195 µm pitch, elevation focus 20 mm). The linear array is used for both ultrasound pulse-echo imaging and photoacoustic signal reception. A diode-pumped laser 104 (e.g., TECH-1053 Specific, Laser-Export Co. Ltd.) delivers 10-ns pulses with a pulse energy of 1.9 mJ at a wavelength of 1053 nm with a 2.8-mm beam diameter, resulting in a fluence of 31 mJ/cm$^2$ at the sample surface. This fluence is well below safety limits, 100 mJ/cm$^2$, at this wavelength. It will be appreciated by persons of skill in the art that suitable laser systems have the advantage of compact size and low cost. The maximum pulse repetition rate in this embodiment is 100 kHz, with maximum output pulse energy of about 2.2 mJ at 1 kHz.

The beam from the laser 104 is directed to a galvanometer scanner 106, referred to herein as a galvo-mirror (e.g., GVS001, Thorlabs Inc.). In this embodiment the mirror angle for the scanner 106 is varied between −1° and +1° using a sinusoidal waveform delivered by a function generator 122 (e.g., AFG 3252, Tektronix Inc.). At a distance of 30 cm from the target this angular range yields a lateral scanning range of about 1 cm. In another embodiment the galvo-mirror angle is varied using a triangle waveform, to produce a more uniform coverage of the image region.

Two constraints when choosing the illumination condition are: 1) the laser fluence should be below safety-related wavelength-dependent thresholds (e.g., 100 mJ/cm$^2$ at 1053 nm wavelength) for a single laser pulse, and 2) the average power should be under 1 W/cm$^2$ at every sample point. For example, to meet real-time frame rates (e.g., 30 Hz or greater), the fluence is limited to 33 mJ/cm$^2$ (1 W/cm$^2$/30 Hz) because the laser spot returns to the same position every 1/30 seconds. A tradeoff between SNR (related to fluence) and frame rate was considered in designing the illumination sequence.

In this exemplary system a 30-Hz frame rate (mirror scan rate) is set, with 24 scanning beams 105 over a 1 cm range and a laser pulse repetition rate of 720 Hz. The axial imaging range is set to 2.8 cm. Both the laser 104 and the ultrasound probe 102 are operatively above the test phantom 90 and aligned such that the incident plane of the laser light 105 and the ultrasound probe imaging plane 103 intersect at a target depth 107. In this embodiment the laser 104 is configured such that the beams 105 are tilted by about 45° with respect to the ultrasound probe 102.

The clinical applicability of this system 100 is demonstrated for needle guidance by providing substantially real-time imaging of needle 96 insertion into a test phantom comprising a chicken breast 92 (approximately 3 cm in thickness). The chicken breast 92 was surrounded by a 10% acoustically and optically transparent gelatin shell 94 (1 cm thickness) for ultrasound coupling. An 18-gauge needle 96 (e.g., 1.27-mm outer diameter, 18G1, Becton Dickinson & Co., East Rutherford, N.J.) is mounted on a linear stage (not shown) for insertion laterally into the test phantom 90 with a tilt angle of about 20°. The target depth in this embodiment is up to 12 mm inside the biological tissue (i.e., chicken breast 92). With a laser light-tissue incident angle of 45°, the light propagation path into the chicken breast 92 is about 17 mm. To demonstrate the real-time imaging capability of the system 100, the insertion of the needle 96 and the injection through the inserted needle 96 of an ink solution (e.g., 44011, Higgins Ink, Leeds, Mass.) are imaged, simulating delivery of a therapeutic agent such as a small molecule drug, combined with a molecularly absorbing dye. The ink solution had an optical absorption coefficient of 20 cm$^{-1}$ at 1053 nm.

A block diagram of the system is shown in FIG. 2. A programmable ultrasound scanner 110 (e.g., Vantage, Verasonics Inc., Redmond, Wash.) is used for all image data acquisition and reconstruction (photoacoustic and ultrasound). The system 100 is operated using Matlab® (The MathWorks Inc., Natick, Mass.) on a conventional computer 120. The computer 120 controls ultrasound and photoacoustic transmits, receives, and data transfer events. A function generator 122 is used to synchronize all operations (i.e., laser pulses, photoacoustic signal recording, and mirror position). In addition to sending a control function signal (e.g., a sine wave signal) to drive the galvo-mirror 106, it sends triggers to the laser 104 and the ultrasound scanner 110 simultaneously to synchronize photoacoustic signal recording with each laser pulse. During one period of the sine wave, multiple laser pulses (i.e., multiple trigger signals) are emitted, covering the entire lateral imaging range (e.g., approx. 1 cm). After each laser pulse and photoacoustic signal recording, several ultrasound pulse-echo beams are formed. The transmit ultrasound pulse selected for this embodiment has a center frequency of 7.8 MHz, and the sampling frequency on receive is 31.25 MHz with a bandwidth of twice the center frequency.

To optimize the frame rate, a large data set (corresponding to several mirror cycles) is acquired and then transferred at once, while the next data set is being acquired, providing continuous data acquisition, as discussed in more detail below.

The particular parameters and exemplary components identified herein are disclosed to provide a detailed disclosure of a particular embodiment to aid persons of skill in the art in understanding the invention. Other parameters and similar components will be apparent to such persons of skill in the art, and the present invention is not limited to these particulars.

An exemplary sequence of steps for scanning an internal region of interest 150 within a body 152 in accordance with the present invention is shown in FIGS. 3A-3F. In this example the internal region of interest 150 is disposed at a depth D from a surface 154 of the body 152. For example, the depth D may be in the range of 1-6 cm from the outer surface 154. In another example, the depth D may be about 2-4 cm from the outer surface 154 of the body 152.

Figure 3A:
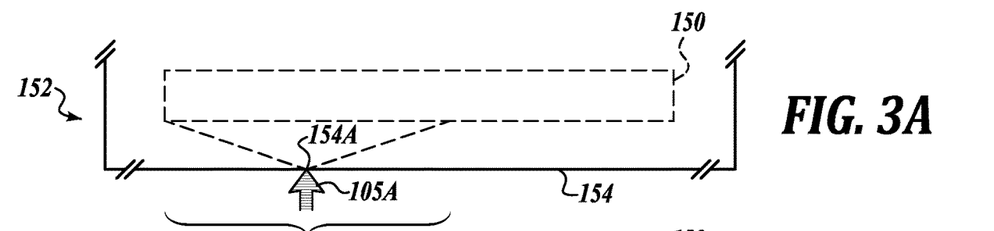
FIGS. 3A-3F illustrate a portion of a laser and ultrasound scanning sequence for the imaging system shown in FIG. 1.

A first location 154A on the outer surface 154 is irradiated with a small-diameter, low-pulse-power laser pulse 105A that is configured to irradiate at least a portion of the internal region of interest 150, inducing a photoacoustic response 155A (FIG. 3A). Although the pulse-power of the laser 154A is low, the laser beam is sufficiently narrow at the outer surface 154 that a high-SNR can be obtained. However, it will be appreciated that due to high optical scattering in tissue a significant portion of the region of interest 150 is irradiated. A plurality of ultrasound pulse-echo beams 156A are then sequentially directed towards the outer surface 154 and region of interest 150, and corresponding ultrasound reflection signals 157A of the ultrasound beams 156A are obtained (FIG. 3B).

Figures 3B, 3C:
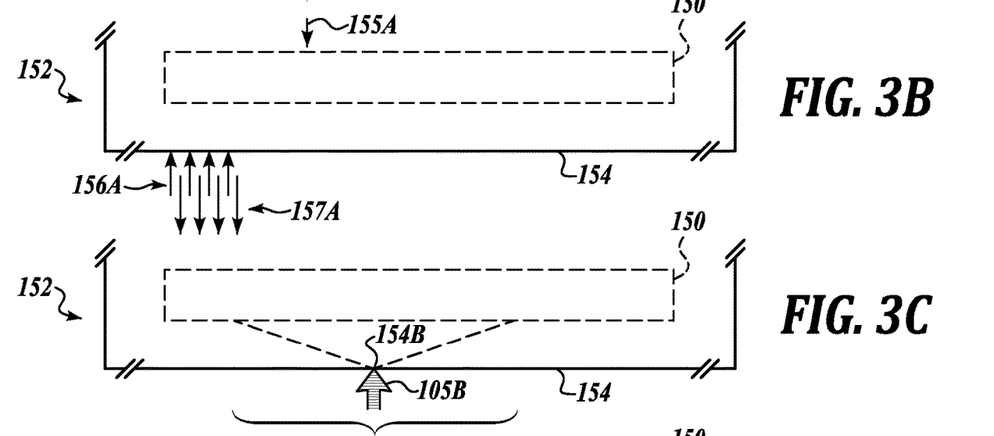
Figures 3D, 3E:
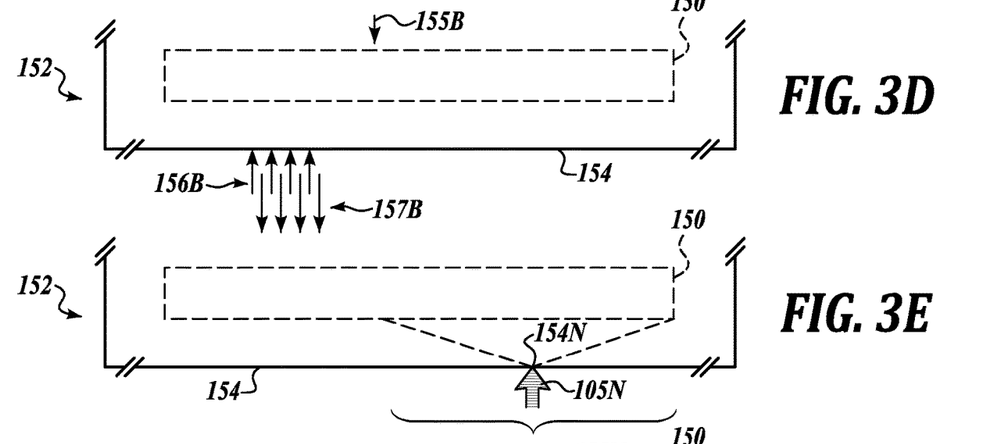
Figure 3F:
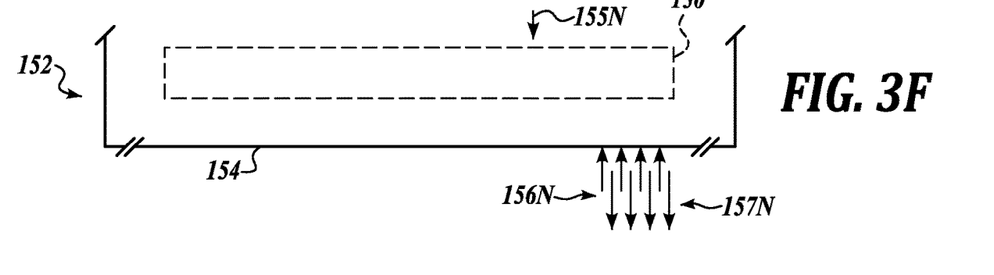

A second location 154B on the outer surface 154 is then irradiated with the similar laser pulse 105B, inducing another photoacoustic response 155B (FIG. 3C). A second plurality of ultrasound beams 156B are then sequentially directed towards the outer surface 154 and region of interest 150, and corresponding ultrasound reflections 157A are obtained (FIG. 3D).

The process is repeated during the scan (FIGS. 3E and 3F), wherein a predetermined nth laser pulse 154N irradiates an nth location 154N on the outer surface 154, producing a photoacoustic response 155N. A series of ultrasound beams 156N are subsequently directed sequentially to the outer surface 154, and ultrasound reflections 157N are obtained, completing one-half of a mirror cycle.

The photoacoustic signals for each cycle are combined to produce photoacoustic sub-frames, and the corresponding pulse-beam ultrasound signals are combined to produce ultrasound sub-frames. The photoacoustic sub-frames and the ultrasound sub-frames are combined to produce a substantially real-time image of the region of interest that combines the advantages of photoacoustic imaging with the advantages of ultrasound imaging.

Figure 4:
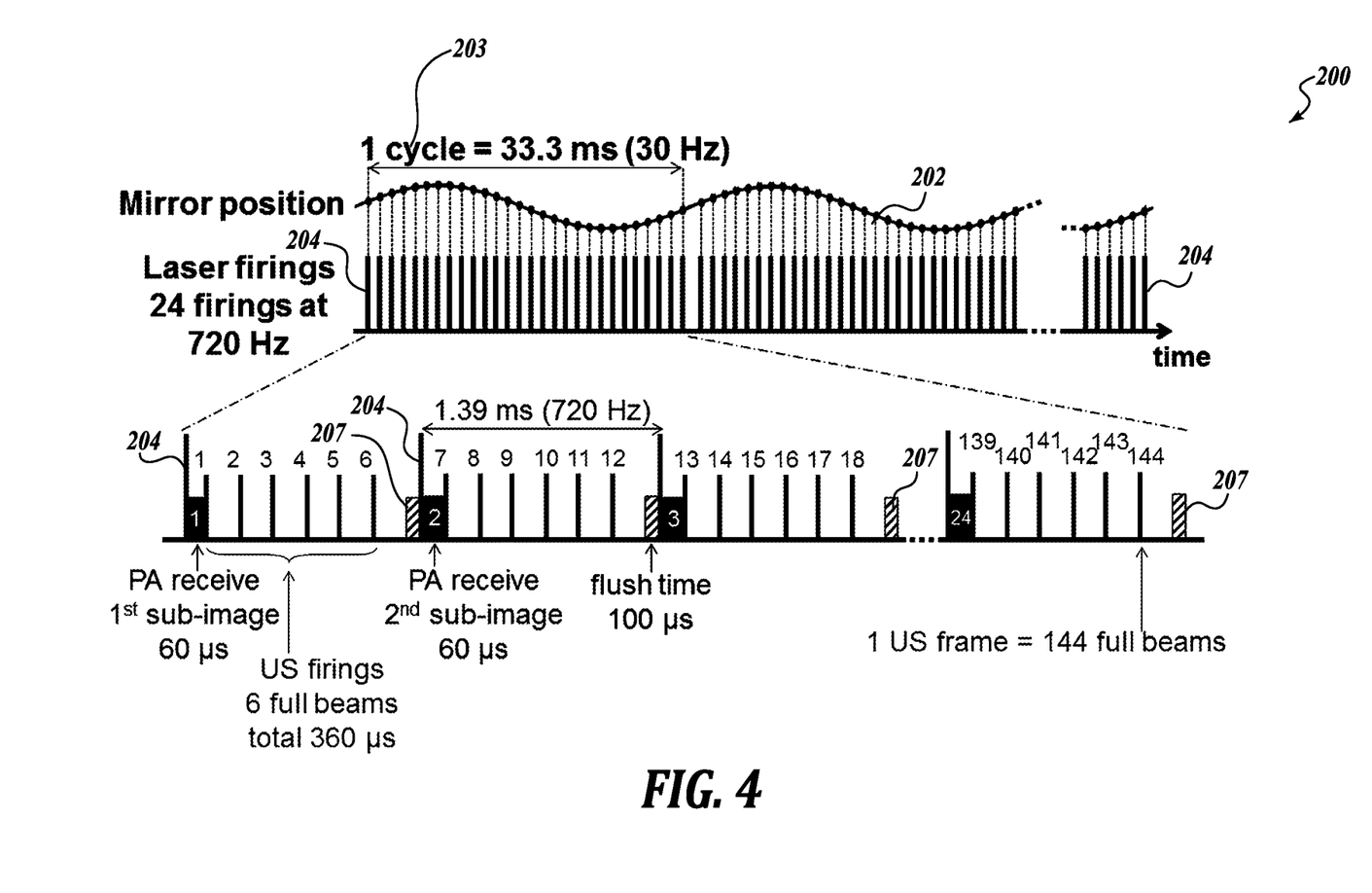
FIG. 4 is a detailed timing diagram for interleaved photoacoustic/ultrasound real-time imaging for the system shown in FIG. 1.

An exemplary detailed timing diagram 200 of the acquisition for one data set is shown in FIG. 4, wherein the system 100 runs continuously by repeating this acquisition set. The timing diagram 200 illustrates the mirror position 202 for one acquisition set comprising a plurality of mirror cycles 203 that scan the pulsed laser beams 105 over the region of interest. One mirror cycle 203 in this example comprises 24 laser pulses or pulses 204, followed immediately by photoacoustic signal acquisition. Each laser pulse 204 (and photoacoustic signal recording) is followed by a plurality of (six in this example) ultrasound pulse-echo ultrasound beams (labelled 1-6, 7-12, 13-18, 139-144) in FIG. 4. Therefore, one mirror cycle 203 produces one photoacoustic frame with 24 sub-frames, and one ultrasound frame from 144 sub-frames. One mirror cycle 203 is completed in 33.3 ms, resulting in an integrated frame rate of 30 Hz.

The number of mirror cycles constituting one data set is selectable and is limited by the maximum amount of data that can be transferred at once by the hardware of the ultrasound scanner 110. For each mirror cycle 203, there are 24 laser pulses for photoacoustic receives (128 channels for each laser pulse). Each laser pulse/photoacoustic receive is followed by six full beams of pulse-echo ultrasound focused at six different adjacent lateral locations. Laser pulses are preceded by adding a flush time 107 (no operation, e.g., 100 µs in current embodiment) to prevent ultrasound emissions from interfering with photoacoustic signal recording. This pattern is repeated until one mirror cycle is completed, allowing the laser beam to cover the entire lateral imaging range twice, and leads to: (i) one integrated photoacoustic frame, resulting from a total of 24 laser pulses at a 720 Hz repetition rate (i.e., 24 single shot sub-frames); and (ii) one integrated ultrasound frame consisting of 144 ultrasound pulse-echo focused beams swept laterally across the imaging range, similar to conventional B-mode ultrasound imaging.

In this embodiment the ultrasound scanner 110 data transfer time from the front end to the host computer 120 memory is determined by a transfer rate of 6600 MB/s and also includes a few milliseconds (typically 5 ms) overhead for each transfer. To reduce the number of transfers, a large data set is acquired and transferred together. The data sets are acquired continuously; while one data set is transferred, the next one is acquired. Parameters are selected such that the data transfer time is shorter than the acquisition time, to allow for continuous data acquisition and real-time imaging.

In such a continuous mode, the frame rate is governed by the galvo-mirror 106 period. One mirror cycle lasts 24/720 Hz=33.33 ms, which corresponds to a frame rate of 30 Hz for an integrated photoacoustic/ultrasound frame for a field of view of 2.8×2.8 cm (lateral×axial). The laser 104 scan range does not cover the whole photoacoustic image range. Nevertheless, light scattering in tissue allows for almost homogeneous irradiation at a few millimeters depth and may cover the entire image range at the imaging depth (e.g., ~1 cm or greater). Both photoacoustic and ultrasound images were reconstructed using a delay-and-sum beam forming approach, Hilbert transformed, with the envelope displayed on a logarithm scale. A fusion image was also obtained by overlaying a photoacoustic image on the top of the corresponding ultrasound image (i.e., add photoacoustic pixel value to corresponding ultrasound pixel and display with different color mapping).

Detailed results from the system 100 and method discussed above are provided in C.-W. Wei, et al., "Real-Time Integrated Photoacoustic and Ultrasound (PAUS) Imaging System to Guide Interventional Procedures: Ex Vivo Study", IEEE Transactions on Ultrasonics, Ferroelectrics, and Frequency Control, Vol. 62, No. 2, February 2015, which is hereby incorporated by reference.

The results illustrate the system 100 and method provide real-time images showing the needle 96 entering the tissue 92, retracting within the tissue 92, and injecting the ink marker into the tissue 92.

With ultrasound imaging alone the image of the needle 96 is only slightly brighter than the tissue 92, with limited contrast because of background scattering. The needle 96 is barely distinct from the trace in static ultrasound images. In contrast to ultrasound, the integrated photoacoustic image exhibits more than 30 dB contrast over the background. Two disconnected segments of the needle are visible in the integrated image and correspond to the geometry and structure of the needle 96, with a tilted injection hole at the needle 96 front. The top segment corresponds to the top edge of the needle 96, and the lower and shorter segment is the lower tip under the hole, with the proximal part not seen because light was blocked by the top needle edge. The rim of the hole has a weaker signal because it was away from the image plane in the elevational direction.

To fully mimic an interventional procedure using a needle, injection of an absorptive agent was imaged ex vivo. A movie showing the needle 96 entering a piece of chicken breast tissue 92, injecting ink solution, and exiting from the tissue 92 was generated, with four sections, corresponding to: (i) inserting the needle 96 into the phantom 90 from a top right corner at an angle of about 20° towards the lower left corner, to a maximum depth of about 22 mm (12 mm below the tissue surface); (ii) retracting the needle 96 until the tip is at a depth of about 18 mm; (iii) injecting the ink solution; and (iv) removing the needle 96 from the tissue 92.

Right after injection, the needle tip 96 is clearly seen in the combined photoacoustic image/ultrasound image. Reverberation artifacts (i.e., multiple reflections) are also observed Ink pours out and diffuses to the volume surrounding the tip, and then flows through the channel in the tissue 92 created when the needle 96 was inserted. At the end of the injection, the diffused ink masks the needle tip 96. The contrast of the needle/injected ink to the tissue 92 background on the combined photoacoustic/ultrasound image is more than 30 dB with a laser penetration distance of more than 1 cm, demonstrating the feasibility of real-time photoacoustic/ultrasound image-guided drug delivery.

A wavelength of 1053 nm was chosen in this study because it provides good penetration and high contrast among commonly used wavelengths (700 to 1100 nm) in photoacoustic imaging. For needle guidance, the optical wavelength is not critical because of the strong optical absorption in metals over the whole therapeutic range of wavelengths. In addition, inexpensive, compact, high powered, fast commercial fiber or diode-pumped lasers operating at this wavelength are available, making clinical translation easier. Wavelength-tunable laser systems enabling spectroscopic imaging, such as the Opolette HR 532 (Opotek Inc., Carlsbad, Calif.) with length >60 cm including power unit+laser head, and versaScan OPO (Newport Corp., Irvine, Calif.) with length ~30 cm, are also available, and the scanning approach can be easily implemented using these laser systems. Compared with these laser systems, usually requiring an additional pumping laser, however, a single-wavelength system is still more compact. For example, exogenous absorbers contain a magnetic component and thus can be magnetically manipulated. By detecting the magnetically induced changes (e.g., displacement), exogenous absorbers can be differentiated from endogenous ones, which are insensitive to the magnetic field.

Although single-wavelength imaging in the region around 1 μm will have many applications, a robust photoacoustic molecular imaging system will benefit from wavelength tunability. In another embodiment the laser 110 is a wavelength-tunable laser, as are known in the art. Leveraging the same laser diode-pumped technology exploited here to serve as the pump for an optical parametric oscillator is contemplated for a system operating at high pulse repetition rates.

Figure 5:
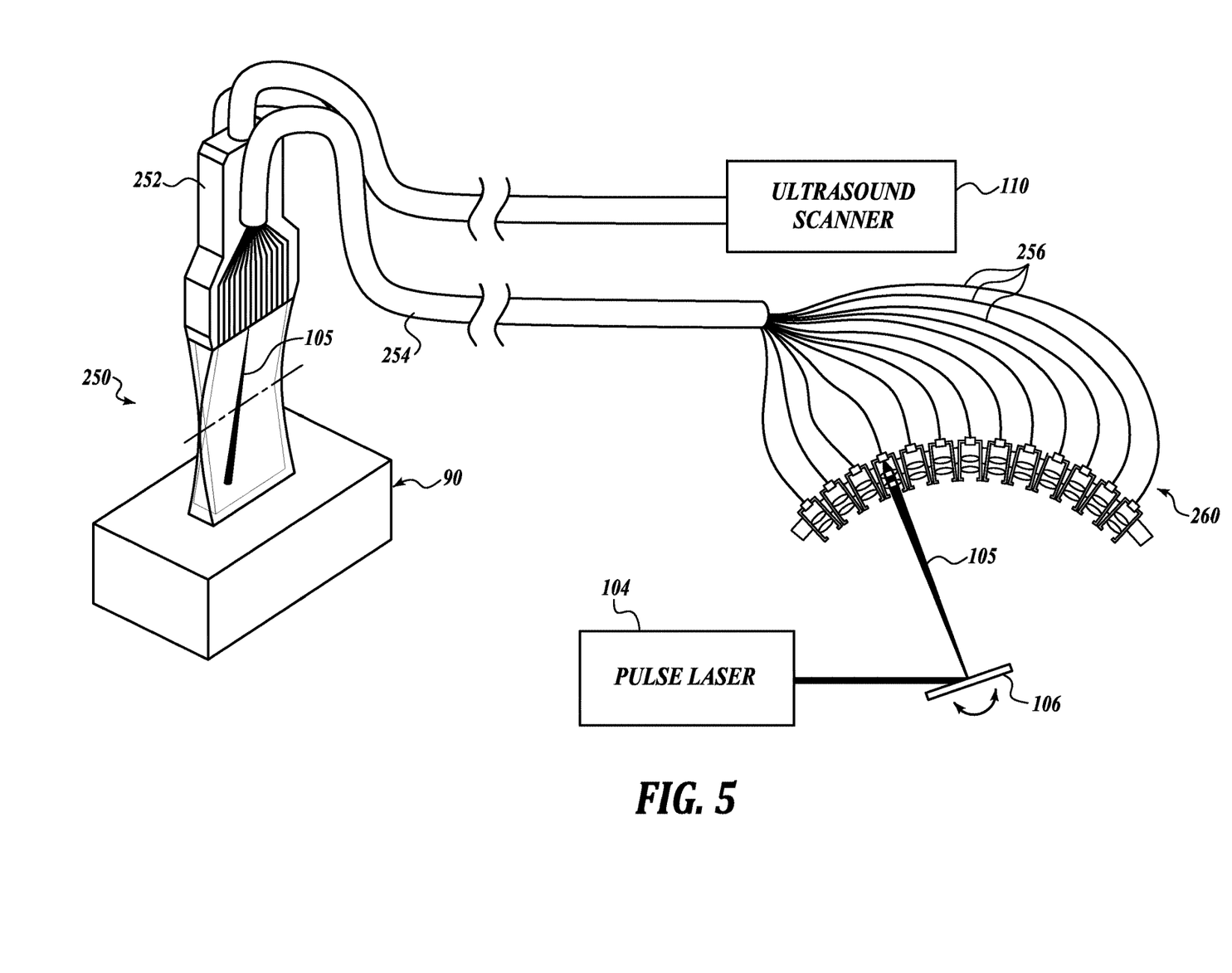
FIG. 5 shows schematically a second embodiment of an integrated photoacoustic and ultrasound imaging system in accordance with the present invention, wherein the laser pulses are transmitted to the ultrasound probe through a fiber optic cable.

In the current embodiment the laser beam 104 angle is at a relatively large angle (approximately 45 degrees) with respect to the ultrasound imaging plane defined by the ultrasound scanner 110. In another embodiment a fiber-optic system 250 is combined with the ultrasound probe 102 in an integrated photoacoustic/ultrasound probe 252, as shown in FIG. 5. The laser pulse 104 is distributed to a fiber bundle 254 that transmits the laser pulse along either, or preferably both, sides of a conventional ultrasound array (e.g., on both sides of the elevation aperture) to optimally illuminate the image plane. The narrow beam laser pulse from the high repetition-rate laser 104 is distributed sequentially to different fibers 256 in the bundle 154 to sweep the small-diameter laser beam over the surface of the body. The sweep is achieved, in this exemplary embodiment, in a remote switching unit 260 in which the laser 104 output is injected to a different fiber 256 on each laser pulse.

The disclosed narrow-beam scanning approach provides image quality that is substantially equivalent to the image quality achievable using a broad-beam irradiation for the same illumination area. The photoacoustic images are summed coherently, i.e., raw wave field after delay-and-sum beam forming but before Hilbert transformation. Because delay-and-sum is a linear operation, summing the wave field for each narrow laser beam is equivalent to the reconstructed wave field generated by a broad beam summed with all the narrow beams (Huygens-Fresnel principle). For imaging a fast-moving object, motion artifacts may be present. Nevertheless, no significant artifact should be observed because light is highly scattered at the imaging depth (~1 cm) and the illumination patterns from multiple beams overlap over the 1-cm scan range.

The frame rate is currently limited by the laser average power regulation, 1 W/cm$^2$, as mentioned above. To reach a frame rate larger than 30 Hz, the laser fluence must be smaller than 33.33 mJ/cm$^2$. For a higher frame rate, the fluence decreases and thus image SNR degrades. Nevertheless, with a high SNR (>35 dB for needle guidance), it is possible to increase the frame rate at the price of lower laser fluence (lower SNR), e.g., 50 Hz frame rate and 20 mJ/cm$^2$ fluence. Also, in the current setup, the mirror scans from one end to the other and returns within one cycle, so two full photoacoustic frames can be formed, instead of one. Therefore the frame rate may be doubled, albeit with the SNR degraded by 3 dB (½). An alternate way is to scan in two dimensions with an additional galvo mirror to scan elevationally, in addition to lateral scanning, i.e., zigzag scan. The laser beam will not return to the same spot at each lateral scan cycle. The fluence can be kept constant while the laser PRF is increased and, thus, the frame rate increased.

The unique mechanism of optical absorption-based contrast makes photoacoustic imaging an ideal modality for molecular imaging, while ultrasound can show simultaneous anatomical landmarks, providing context for molecular measurements. A particular example is to detect circulating tumor cells in blood vessels, providing a critical indicator of metastasis for cancer. Metastatic tumor cells circulating in the vasculature can be accumulated and detected using a composite nanosystem exhibiting both strong magnetic properties and high optical absorption at a desired wavelength. By targeting these particles to specific biomarkers on tumor cells, circulating tumor cells can be trapped and manipulated with an external magnetic system and non-invasively imaged using the integrated photoacoustic/ultrasound imaging disclosed herein. The imaging site is chosen at the radial artery in the forearm, which has a diameter of 1 to 2 mm and a level of 10 mL/min flow rate and, thus, a reasonable examination time to interrogate a significant blood volume. The accumulated cells create heterogeneous photoacoustic sources inside vessels, and thus can be detected by a commercial ultrasound probe with a narrow frequency band. In short, the system presented in this paper is well-suited to clinical translation of this technology.

While illustrative embodiments have been illustrated and described, it will be appreciated that various changes can be made therein without departing from the spirit and scope of the invention.

The embodiments of the invention in which an exclusive property or privilege is claimed are defined as follows:

1. A method for generating a combined photoacoustic and ultrasound image frame of an internal region of a body having an external surface, the method comprising:
   performing in sequence, to generate an image frame of the internal region of the body:
   irradiating a first location on the external surface with a first laser pulse such that the first laser pulse irradiates a first section of the internal region of the body;

receiving a first photoacoustic response to the first laser pulse, and using the received first photoacoustic response to generate a first photoacoustic sub-frame of the internal region of the body;

sequentially transmitting a first plurality of ultrasound pulse-echo beams to scan the first section of the internal region of the body;

receiving a first set of ultrasound reflections of the first plurality of ultrasound pulse-echo beams and using the received first set of ultrasound reflections to generate a first set of ultrasound sub-frames of the internal region of the body;

irradiating a second location on the external surface with a second laser pulse such that the second laser pulse irradiates a second section of the internal region of the body, wherein the second location on the external surface is different from the first location on the external surface;

receiving a second photoacoustic response to the second laser pulse, and using the received second photoacoustic response to generate a second photoacoustic sub-frame of the internal region of the body;

sequentially transmitting a second plurality of ultrasound pulse-echo beams to scan the second section of the internal region of the body, wherein the second section of the internal region of the body is different from the first section of the internal region of the body;

receiving a second set of ultrasound reflections of the second plurality of ultrasound pulse-echo beams, and using the received second set of ultrasound reflections to generate a second set of ultrasound sub-frames of the internal region of the body;

combining the first and second photoacoustic sub-frames to generate a photoacoustic frame of the internal region of the body, and combining the first and second sets of ultrasound sub-frames to generate an ultrasound frame of the internal region of the body; and combining the photoacoustic frame and the ultrasound frame to generate the image frame of the internal region of the body.

2. The method of claim 1, wherein the first laser pulse and the second laser pulse have energies of less than 10 millijoules.

3. The method of claim 1, wherein the first laser pulse and the second laser pulse have energies of less than 2 millijoules.

4. The method of claim 1, wherein the first laser pulse and the second laser pulse each have a diameter that is less than 3 mm.

5. The method of claim 1, wherein the first laser pulse has a wavelength between 400 nm and 1500 nm, and further wherein the first laser pulse has a fluence that is less than a wavelength-dependent maximum fluence that would damage tissue.

6. The method of claim 1, wherein the first laser pulse and the second laser pulse have a pulse fluence less than 100 mJ/cm$^2$.

7. The method of claim 1, wherein the first plurality of ultrasound pulse-echo beams comprise at least six pulse-echo beams.

8. The method of claim 1, wherein the first and second laser pulses are produced by a laser diode-pumped Q-switched laser.

9. The method of claim 1, wherein the first plurality of ultrasound pulse-echo beams is generated with an ultrasound linear array.

10. The method of claim 9, wherein the ultrasound linear array receives the first and second photoacoustic responses and the first and second sets of ultrasound reflections.

11. The method of claim 9, wherein the ultrasound linear array is disposed in a probe, and further wherein the first and second laser pulses are emitted from the probe.

12. The method of claim 11, wherein the probe comprises a distal face configured to be positioned against the body, and wherein a plurality of optical fibers are configured to transmit the first and second laser pulses from a laser to the distal face of the probe.

13. The method of claim 12, wherein a remote switching unit distributes the first and second laser pulses to selected ones of the plurality of optical fibers.

14. The method of claim 12, wherein the plurality of optical fibers extend along both sides of the ultrasound linear array.

15. The method of claim 1, further comprising (i) irradiating additional locations on the external surface with additional laser pulses, (ii) receiving corresponding photoacoustic responses and generating additional photoacoustic sub-frames; (iii) sequentially transmitting additional pluralities of ultrasound pulse-echo beams towards the additional sections of the internal region of the body, (iv) receiving corresponding ultrasound reflections and generating additional sets of ultrasound sub-frames of the internal region of the body, (v) including the additional photoacoustic sub-frames with the first and second photoacoustic sub-frames to generate the photoacoustic frame, and including the additional ultrasound sub-frames with the first and second ultrasound sub-frames to generate the ultrasound image frame.

16. The method of claim 15, wherein the number of additional locations comprise at least twenty-two additional locations.

17. A method for generating a real-time video of the internal region of the body, wherein the method of claim 1 is used to generate a sequence of image frames of the internal region of the body, and displaying the sequence of images as frames of the real-time video.

18. A combined photoacoustic and ultrasound imaging system for imaging an interior region of a target, the system comprising:

an ultrasound linear array configured to generate ultrasound pulses, to receive and process ultrasound reflection data, and to receive and process photoacoustic signals;

a laser configured to generate narrow-beam laser pulses having a pulse energy of less than 5 mJ;

a laser pulse distributor configured to receive laser pulses from the laser and to direct the pulses to a plurality of locations on a target;

a computer system configured to control the ultrasound linear array, the laser, and the laser pulse distributor, to receive processed ultrasound reflection data and photoacoustic signals from the ultrasound linear array, and to generate combined photoacoustic and ultrasound images from the received data and signals, wherein the system is configured to generate a combined photoacoustic and ultrasound image frame of the interior region of the target using the method of claim 1.

19. The imaging system of claim 18, wherein the laser pulse distributor comprises a switching unit in which laser pulses from the laser are directed sequentially into a plurality of fibers that extend into a probe containing the ultrasound linear array.

* * * * *